US012738372B2

(12) United States Patent
Koster et al.

(10) Patent No.: US 12,738,372 B2
(45) Date of Patent: Sep. 15, 2026

(54) POST-SERVICE STATE VALIDATOR FOR MEDICAL DEVICES

(71) Applicant: KONINKLIJKE PHILIPS N.V., Eindhoven (NL)

(72) Inventors: Robert Paul Koster, Eindhoven (NL); Ramon Antoine Wiro Clout, Eindhoven (NL); Sauvik Bhattacharya, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 6 days.

(21) Appl. No.: 18/709,184

(22) PCT Filed: Nov. 17, 2022

(86) PCT No.: PCT/EP2022/082312
§ 371 (c)(1),
(2) Date: May 10, 2024

(87) PCT Pub. No.: WO2023/099234
PCT Pub. Date: Jun. 8, 2023

(65) Prior Publication Data

US 2025/0006356 A1 Jan. 2, 2025

Related U.S. Application Data

(60) Provisional application No. 63/284,073, filed on Nov. 30, 2021.

(30) Foreign Application Priority Data

Mar. 22, 2022 (EP) .................................... 22163560

(51) Int. Cl.
*G16H 40/40* (2018.01)
*G16H 40/60* (2018.01)

(52) U.S. Cl.
CPC ............. *G16H 40/40* (2018.01); *G16H 40/60* (2018.01)

(58) Field of Classification Search
CPC ............................... G16H 40/40; G16H 40/60
See application file for complete search history.

(56) References Cited

U.S. PATENT DOCUMENTS

2011/0214186 A1* 9/2011 Khilnani .............. G06F 21/575 726/24
2014/0032232 A1 1/2014 Brown
(Continued)

FOREIGN PATENT DOCUMENTS

CN 108899082 A1 11/2018
CN 109102189 A 12/2018
(Continued)

OTHER PUBLICATIONS

Fangyu Li, Assessing the Accuracy of Diagnostic Tests, 2018, p. 207-208 (Year: 2018).*
(Continued)

*Primary Examiner* — Ibrahim N El-Bathy

(57) ABSTRACT

A non-transitory computer readable medium (107, 127) stores instructions readable and executable by at least one electronic processor (101, 113) to provide an operating mode for a medical device (120) to provide medical diagnostic and/or medical treatment functionality; instructions readable and executable by the at least one electronic processor to provide a service mode for the medical device that provides service functions for servicing the medical device; and instructions readable and executable by the at least one electronic processor to: perform a validation process at an end of a servicing session of the medical device performed using the service mode to determine whether the medical device is in an incorrect operating state; and display, on a display device (105) operable by a service engineer and (Continued)

in response to determining the medical device is in the incorrect operating state, an indication that the medical device is in the incorrect operating state.

20 Claims, 2 Drawing Sheets

(56) References Cited

U.S. PATENT DOCUMENTS

| | | | | |
|---|---|---|---|---|
| 2015/0371198 | A1* | 12/2015 | Jensen | G06F 3/04842 705/305 |
| 2017/0124334 | A1 | 5/2017 | Thom | |
| 2018/0165143 | A1 | 6/2018 | Hayashi | |
| 2020/0210966 | A1 | 7/2020 | Nuthi | |
| 2021/0019413 | A1 | 1/2021 | Deck | |
| 2021/0335479 | A1* | 10/2021 | Liang | G16H 40/40 |
| 2023/0213610 | A1* | 7/2023 | Eberspach | G06V 40/166 |
| 2024/0321439 | A1* | 9/2024 | Danielsen | G16H 40/40 |

FOREIGN PATENT DOCUMENTS

| | | | |
|---|---|---|---|
| CN | 110268425 | A | 9/2019 |
| JP | 2021526250 | A | 9/2021 |
| WO | 2021/064194 | A1 | 4/2021 |

OTHER PUBLICATIONS

International Search Report and Written Opinion Dated Mar. 14, 2023 For International Application No. PCT/EP2022/082312 Filed Nov. 17, 2022.

* cited by examiner

POST-SERVICE STATE VALIDATOR FOR MEDICAL DEVICES

CROSS REFERENCE TO RELATED APPLICATIONS

This application is the U.S. National Phase application under 35 U.S.C. § 371 of International Application No. PCT/EP2022/082312 filed Nov. 17, 2022, which claims the benefit of European Patent Application Number 22163560.0 filed Mar. 22, 2022 and U.S. Provisional Patent Application No. 63/284,073 filed Nov. 30, 2021. These applications are hereby incorporated by reference herein.

FIELD OF THE INVENTION

The following relates generally to the medical device maintenance arts, medical imaging device maintenance arts, medical device maintenance and validation arts, and related arts.

BACKGROUND OF THE INVENTION

Customer services for medical imaging systems, such as magnetic resonance imaging (MRI), a computed tomography (CT), a positron emission tomography (PET), interventional radiology (IR), or other medical imaging systems, or for other types of medical devices such as a mechanical ventilator, a multifunction patient monitor, a radiation therapy device, or so forth, can require reactive, proactive, and predictive maintenance services. Because these services rely heavily on data, availability of a reliable infrastructure that acquires, processes and stores data from medical systems and other sources is crucial. When there is a problem with a medical system, customers can report the issue to the customer service center via various channels (e.g., by phone, customer portal or mobile application). Then, service engineers (SEs—which can include remote SEs (RSEs) and field SEs (FSEs)) can perform system diagnostics to identify the root-cause of the problem and resolve the issue. Both activities may be performed remotely or on-site, by different SEs. In addition to reactive maintenance as described above, proactive, and predictive diagnostic models are built to identify failure of a system or a part of a system. The output of the diagnostic models is communicated to RSEs, in a form of alert, using a service delivery platform. The RSEs act on the alerts to provide maintenance services.

Customers can call a manufacturer of the medical device, or other maintenance service provider, when they encounter an issue. An RSE troubleshoots the issue to find a possible solution remotely and/or assigns the right field service engineer to go onsite. A fixed number of RSEs are typically assigned per day to resolve all issues reported by customers. One RSE is assigned to resolve one issue at a time.

Such medical imaging devices and other medical devices (or even more generally, electronic devices) may have a service mode that provides the SE with diagnostic, testing, and/or other functionality different from normal operations functionality. Such devices are computerized and sufficiently complex that they are occasionally serviced by expert SE's. In a typical service call, the SE logs into the medical device using appropriate SE credentials, and this brings the electronic controller up in a special service mode providing specialized service menu options. This could include a specialized service mode user interface, or could more simply be a command line interface. The SE performs service, such as installing software, replacing and/or calibrating components, and so forth. Some of these operations may involve taking the medical device out of its usual stable operating state. For example, the SE may need to turn off software or application whitelisting in order to run software that is not on the whitelist. Certain component installation or calibration operations may also require temporarily reconfiguring the medical device for those operations. For example, testing of an X-ray tube might involve raising an upper limit usually imposed to avoid undue X-ray tube filament wear in order to briefly operate the X-ray tube at higher power for testing purposes. After the servicing is complete, the SE should restore the medical device to a stable configuration, for example by reactivating software whitelisting, reconfiguring the device for normal operation, and/or so forth.

However, the SE may fail to place the medical device into a stable operating configuration after completing work. Particularly, there is a chance that the SE may fail to properly reestablish a stable operating configuration in accordance with OEM specifications.

The following discloses certain improvements to overcome these problems and others.

SUMMARY OF THE INVENTION

In one aspect, a non-transitory computer readable medium stores instructions readable and executable by at least one electronic processor to provide an operating mode for a medical device to provide medical diagnostic and/or medical treatment functionality; instructions readable and executable by the at least one electronic processor to provide a service mode for the medical device that provides service functions for servicing the medical device; and instructions readable and executable by the at least one electronic processor to: perform a validation process at an end of a servicing session of the medical device performed using the service mode to determine whether the medical device is in an incorrect operating state; and display, on a display device operable by a service engineer (SE) and in response to determining the medical device is in the incorrect operating state, an indication that the medical device is in the incorrect operating state.

In another aspect, an electronic device comprises at least one electronic processor; and a non-transitory computer readable medium storing instructions readable and executable by the at least one electronic processor to: provide an operating mode user interface (UI) for a medical device that provides operational functions for operating the medical device to provide medical diagnostic and/or medical treatment functionality; perform a validation process at an end of a servicing session of the medical device performed to determine whether the medical device is in an incorrect operating state, wherein the validation process is automatically performed responsive to an input indicating that the servicing session is completed; and display, on a display device operable by the SE and in response to determining the medical device is in the incorrect operating state, an indication that the medical device is in the incorrect operating state.

In another aspect, a method of determining whether a medical device is in an incorrect operating state following a servicing session comprising: providing an operating mode UI for a medical device that provides operational functions for operating the medical device to provide medical diagnostic and/or medical treatment functionality; providing a service mode UI for the medical device that provides service functions for servicing the electronic device; performing a validation process at an end of a servicing session of the medical device performed using the service mode user interface to determine whether the medical device is in an incorrect operating state, wherein the validation process is automatically performed responsive to the medical device entering the operating mode user interface after the servicing session is completed; and displaying, on a display device of a remote electronic processing device operable by the SE and in response to determining the medical device is in the incorrect operating state, an indication that the medical device is in the incorrect operating state.

One advantage resides in ensuring the returning of a medical device to a secure state after a servicing session.

Another advantage resides in ensuring a correct operational mode of a medical device after a servicing session.

Another advantage resides in avoiding unnecessary subsequent servicing sessions of a medical device due to an error in returning the medical device to a correct operational mode after a servicing session, thereby avoiding unnecessary delay and cost.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION OF EMBODIMENTS

The following relates to performing a validation at the end of a servicing session by an SE of a medical device. The validation runs various validation algorithms (referred to as "diagnostic content" herein) that consume information such as machine log data, a record of operations performed by the SE (if available), and a last operational state (if available). Typically, the validation algorithms are specific to the particular type of medical device.

The validation may be run manually, e.g. by having the SE select a validation button before closing and logging out of the service mode. However, in a preferred embodiment the validation is automatically triggered during the closing/logout process, and/or when the medical device re-enters its operational mode.

The validation algorithms may reside locally, on an edge server, and/or on a central manufacturer server. The latter option is preferred as it enables the validation algorithms to be updated centrally and deployed to the installed base. Also, the log data are collected at the central manufacturer server so that is a convenient location.

In one embodiment, the validation algorithms include a check on the anti-virus software updating. This recognizes that anti-virus updating can get out of synchronization, i.e. virus definitions not updating or not updating to the correct version, and as the SE is well positioned to fix that problem having it flagged as part of the validation is beneficial.

Figure 1:
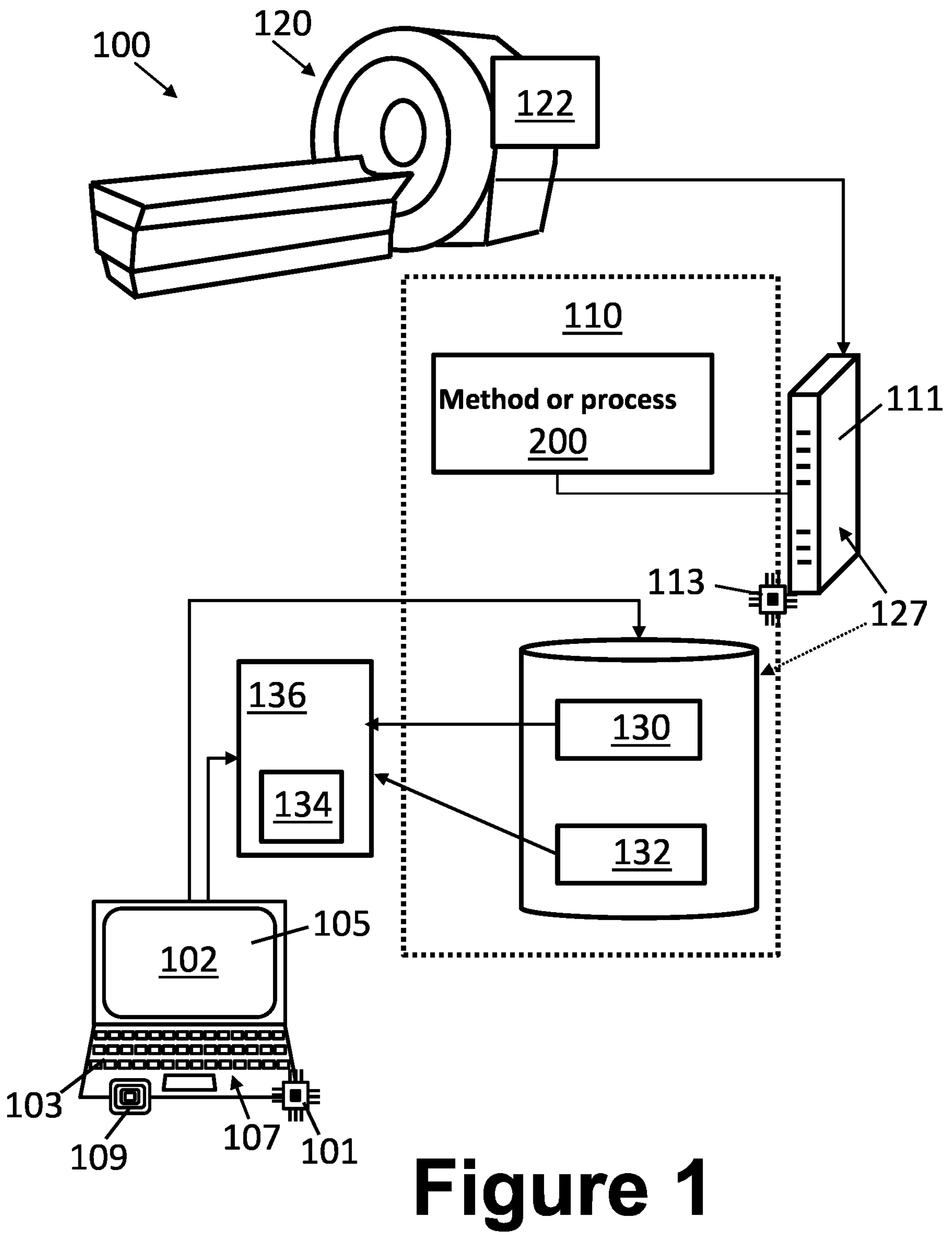
FIG. 1 diagrammatically illustrates an illustrative system for servicing medical device in accordance with the present disclosure.

With reference to FIG. 1, an illustrative servicing support system 100 for supporting a service engineer in servicing an electronic device 120 (e.g., a medical imaging device—also referred to as a medical device, an imaging device, imaging scanner, and variants thereof) is diagrammatically shown. By way of some non-limiting illustrative examples, the medical device under service may be a medical imaging device such as a magnetic resonance imaging (MRI) scanner, a computed tomography (CT) scanner, a positron emission tomography (PET) scanner, a gamma camera for performing single photon emission computed tomography (SPECT), an interventional radiology (IR) device, or so forth; or may be another type of medical device such as a mechanical ventilator, a multifunction patient monitor, a radiation therapy device, or so forth. (More generally, the disclosed approach can be applied in conjunction with any type of computerized device that automatically generates log data that are analyzed by predictive or proactive models to predict or identify component failures, e.g., the approach could be applied to a commercial airliner, factory robot, or so forth).

As shown in FIG. 1, the servicing support system 100 includes, or is accessible by, a service device 102 that may for example be a workstation or electronic processing device used by an RSE. In some embodiments, the service device 102 is the electronic controller of the medical device 120, which is also used for normal operation of the medical device 120. In this case, the medical device controller is typically placed into a service mode that provides access to servicing functions that are not normally used by the medical device operator in operating the medical device 120. For example, the service mode may include a dedicated service mode interface, which could be a graphical user interface (i.e., service mode GUI), although in other embodiments the service mode may provide a simple command line interface. The service device 102 may in other embodiments be a portable device such as a notebook computer or a mobile device (e.g. cellphone) that is carried by a field service engineer (FSE) when visiting the site of the medical device 120 and connects with the controller of the medical device 120 by a wired or wireless communication link. The service device 102 can in other embodiments be a desktop computer or workstation, that is accessed by a remote service engineer (RSE) and connects with the controller of the medical device 120 by the Internet and/or a local area network. In other embodiments, as previously noted, the service device 102 may be an imaging system controller or computer integral with or operatively connected with the imaging device undergoing service (e.g., at a medical facility).

The service device 102 includes a display device 105 via which information is displayed during the servicing, such as a command line for entering commands, a service mode GUI, diagnostic test results, log data retrieved from log files automatically maintained by the medical device 102, and/or so forth. The service device 102 also preferably allows the service engineer to interact with the servicing support system via at least one user input device 103 such a mouse, keyboard, or touchscreen. The service device further includes an electronic processer 101 and non-transitory storage medium 107 (internal components which are diagrammatically indicated in FIG. 1). The non-transitory storage medium 107 stores instructions which are readable and executable by the electronic processor 101 for interfacing with the servicing support system 100. The service device 102 also includes a communication interface 109 to communicate with a backend server or processing device 111, which typically implements the computational aspects of the servicing support system 100 (e.g., the server 111 has the processing power for implementing computationally complex aspects of the servicing support system 100). Such communication interfaces 109 include, for example, a wired and/or wireless Ethernet interface (e.g., in the case in which the service device 102 is a RSE workstation); or in the case in which the service device 102 is a portable FSE device the interface 109 may be a wireless Wi-Fi or 4G/5G interface or the like for connection to the Internet and/or an intranet. Some aspects of the servicing support system 100 may also be implemented by cloud processing or other remote processing (that is, the server computer 111 may be embodied as a cloud-based computing resource comprising a plurality of interconnected servers).

In illustrative FIG. 1, the servicing support system optionally further includes a backend 110 (e.g., implemented and/or owned by the imaging device manufacturer or leased by the manufacturer from a cloud computing service provider). The backend 110 receives log data (e.g., a machine log automatically generated by the medical imaging device 120, a service log for the medical imaging device 120, and/or so forth) on a continuous or occasional basis (e.g., in some setups the imaging device 120 uploads machine log entries to the backend 110 on a daily basis). The backend processing for performing predictive and proactive fault modeling and (as disclosed herein) maintenance service analyses is performed on the backend server 111 equipped with an electronic processor 113 (diagrammatically indicated internal component). The server 111 is equipped with non-transitory storage medium 127 (internal components which are diagrammatically indicated in FIG. 1). While a single server computer is shown, it will be appreciated that the backend 110 may more generally be implemented on a single server computer, or a server cluster, or a cloud computing resource comprising ad hoc-interconnected server computers, or so forth. Furthermore, while FIG. 1 shows a single medical imaging device 120, more generally the database backend 110 will receive log data from many medical imaging devices (e.g., tens, hundreds, or more imaging devices) and performs the disclosed processing for each such medical imaging device.

With continuing reference to FIG. 1, the non-transitory computer readable medium 127 stores instructions executable by the service device 102 (and/or the electronic processor 113 of the backend server 111) to provide an operating mode for the medical device 120. In one embodiment, the operating mode can be accessed by an operator of the medical device 120 via an operating mode user interface (UI) 130 on the display device 105 of the medical device controller of the medical device 120. The operating mode UI 130 provides operational functions for operating the medical device 120 to perform its ordinary medical functionality, such as acquiring medical images in the case of a medical imaging device, or providing respiratory support in the case of a mechanical ventilator, or so forth.

The non-transitory computer readable medium 127 stores instructions executable by the service device 102 (and/or the electronic processor 113 of the backend server 111) to provide a service mode for the medical device 120 that provides service functions for servicing the medical device 120. In one embodiment, the service mode can be provided as a service mode (UI) 132 on the display device 105 of the SE electronic processing device 102. The service mode UI 132 can provide service functions for servicing the medical device 120 with the SE electronic processing device 102. In another embodiment, the service mode UI 132 can be provided on the display device 122 of the controller of the medical device 120. Instead of providing a service mode UI, the service mode may be accessed via a command line, for example via a terminal window opened on the controller of the medical device 120. This can be a sufficient user interfacing mechanism since the service mode functions are not regularly accessed, and the SE is expected to have good familiarity with the software/firmware architecture of the medical device 120. In either type of interfacing, the service mode may optionally entail the SE logging into the controller of the medical device 120 using administrative credentials or the like.

In the service mode, the SE can often perform service functions that are unavailable to the usual operator of the medical device 120. For example, the SE may be able to turn off whitelisting of software, reconfigure components of the medical device 120 in ways not normally employed during usual operation of the medical device 120 for its intended medical functionality, or so forth. These service functions provide enhanced capabilities that are useful for the SE in diagnosing and remedying malfunctions of the medical device 120 or in performing other servicing operations such as replacing components or so forth. However, it has been observed that SEs sometimes fail to restore the medical device 120 to a correct operating state when the servicing is finished. This can lead to an unnecessary follow-up service call to place the medical device 120 back into a correct operating state, or in some cases can even have detrimental impact such as a failure to reinstate whitelisting leaving the controller of the medical device in a vulnerable state.

To address this, as disclosed herein the non-transitory storage medium 127 stores instructions executable by the service device 102 (and/or the electronic processor 113 of the backend server 111) to perform a method 200 of determining whether the medical device 120 is in an incorrect operating state following a servicing session. If an incorrect operating state is detected, the SE can be so notified. In some embodiments, the method 200 will not permit the medical device 120 to be placed back into the operating mode until it is in a correct operating state.

Figure 2:
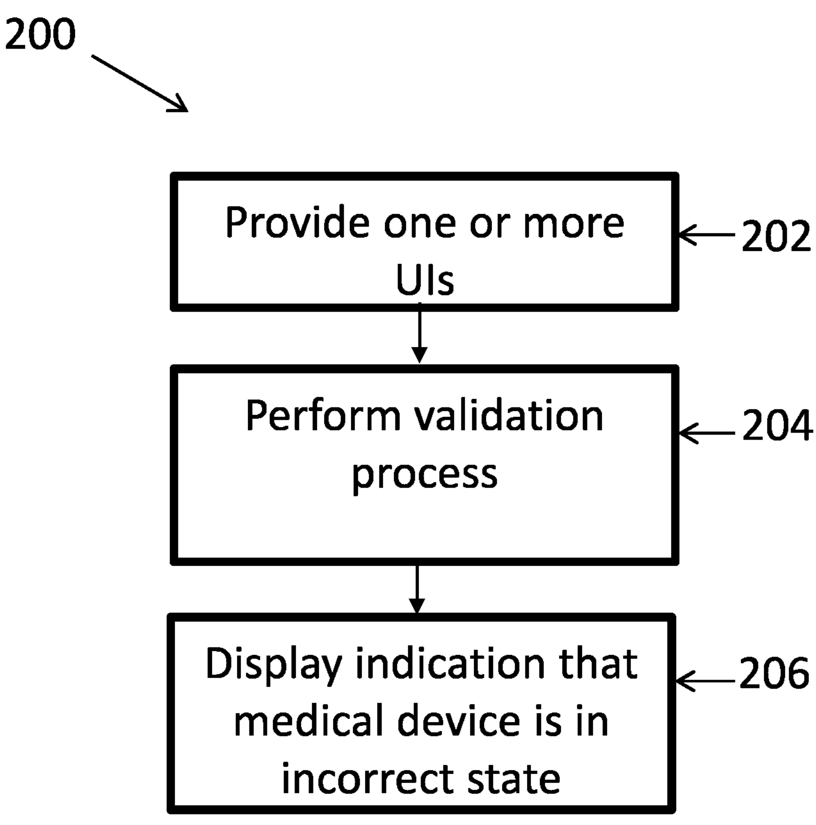
FIG. 2 shows exemplary flow chart operations of the system of FIG. 1.

With continuing reference to FIG. 1 and further reference to FIG. 2, an illustrative embodiment of the method 200 executable by the electronic processor 113 of the backend server 111 is diagrammatically shown as a flowchart. In some examples, the method 200 may be performed at least in part by cloud processing.

To begin the method 200, at an operation 202, the operating mode UI 103 and/or the service mode UI 132 (or otherwise configured service mode, such as a service mode accessed by a command line interface) are provided on the display device 105 of the SE electronic processing device 102 (or on the display device 122 of the medical device 120). The SE enters the service mode and then performs a servicing session on the medical device 120.

At an operation 204, a validation process is performed at an end of a servicing session of the medical device performed using the service mode to determine whether the medical device is in an incorrect operating state. This can be performed in a variety of manners. In some embodiments, the validation process 204 includes determining a state of the medical device 120 by analyzing device data (e.g., log data, configuration data, and so forth) generated by the medical device 120. In other embodiments, the validation process 204 includes determining a state of the medical device 120 by analyzing a record of operations performed during the servicing session. In further embodiments, the validation process 204 includes determining a most-recent correct operational state of the medical device 120, and comparing a current state of the medical device 120 with the most-recent correct operational state of the medical device 120.

In order to perform the validation process 204, in some embodiments, a button 134 selectable by the SE is provided. In some examples, the button 134 can be a mechanical button on the medical device 120. In other examples, the button 134 can be provided on the display device 105 (and selected by the SE via the at least one user input device 103), or on the display device 122 of the medical device 120. In other embodiments, the validation process 204 is automatically performed responsive to an input to the service mode UI 132 indicating that the servicing session is completed. In further embodiments, the validation process 204 is automatically performed responsive to the medical device 120 entering the operating mode (e.g., when the operating mode UI 130 is displayed) after the servicing session is completed. Advantageously, the validation process 204 is performed at the backend database 111, which can be operable by a manufacturer of the medical device 120. This enables a single validation process to be applied to all devices of a similar or same make/model, and thus facilitates updating of the validation process across the deployed fleet of medical devices. However, in other embodiments, the validation process 204 may performed by the service device 102.

The validation process 204 can be used to detect whether the medical device 120 is in a "correct" (i.e., stable) operating state or an "incorrect" operating state after the servicing session. In one example, the validation process 204 includes detecting the incorrect operating state comprising anti-virus software of the medical device 120 failing to update virus signatures. In another example, the validation process 204 includes detecting the incorrect operating state comprising software whitelisting of the medical device 120 being deactivated, or the medical device 120 being left in an unsupported or insecure configuration setting. In another example, the validation process 204 includes detecting the incorrect operating state comprising an incorrectly configured or deactivated firewall of the medical device 120. In another example, the validation process 204 includes detecting the incorrect operating state comprising a configuration of the medical device 120 that is not compatible with operating the medical device 120 to provide the medical diagnostic and/or medical treatment functionality. In another example, the validation process 204 includes detecting the incorrect operating state comprising a missing component (or a component due for replacement) of the medical device 120. These are merely examples, and should not be construed as limiting.

At an operation 206, in response to determining the medical device 120 is in the incorrect operating state, an indication 136 that the medical device 120 is in the incorrect operating state can be displayed. In one example, the indication 136 can be displayed on the display device 105 of the SE electronic processing device 102, while in other examples the indication 136 can be displayed on the display device 122 of the medical device 120.

In some embodiments, as previously noted, the validation process 204 is automatically triggered by exiting the service mode. This ensures the SE does not accidentally forget to run the validation process 204. In such embodiments, the operation 206 may provide further enforcement by not permitting the service mode to be exited until the medical device 120 is placed into a correct operating state. To this end, each time the SE attempts to exit the service mode the validation process 204 is run and, if an incorrect operating state is detected, this is displayed at operation 206 and the medical device remains in the service mode. This sequence repeats until the validation process 204 confirms the medical device 120 is in a correct operating mode, at which point the service mode is exited.

In other embodiments, the validation process 204 is automatically triggered by reentering the operational mode. This again ensures the SE does not accidentally forget to run the validation process 204. In such embodiments, the operation 206 may provide further enforcement by not permitting entry into the operational mode until the medical device 120 is placed into a correct operating state. To this end, each time the SE attempts to enter the operational mode the validation process 204 is run and, if an incorrect operating state is detected, this is displayed at operation 206 and the medical device reverts back to the service mode. This sequence repeats until the validation process 204 confirms the medical device 120 is in a correct operating mode, at which point the operational mode is entered.

EXAMPLES

The following describes the system 100 and the method 200 in more detail. The system 100 can include a state validator to validate that the medical device 120 is in a well-defined state. For this purpose, the state validator uses diagnostic content that when executed or interpreted validates if selected medical device parameters meet pre-defined criteria. The state validator provides feedback to the service engineer if the medical device 120 is not in a well-defined state and optionally also when it is in a well-defined state.

Diagnostic content (e.g. trained machine learning models, scripts, (pattern matching) rules, etc. or a combination thereof) can be obtained. The diagnostic content operates on diagnostic input data. Diagnostic input data can comprise inputs from the medical device 120 such as log and configuration files, internal state, and settings, etc. Diagnostic input data may be obtained from the system through various means including reading from the file system, querying APIs, execute commands, and so forth.

For example, diagnostic content can be an analytical model that raises an alert if the set of firewall rules of the medical device 120 contain one or more rules that are classified as common misconfigurations, anomalous or high risk. Diagnostic content can also be a script that checks if software whitelisting is enabled by checking the Windows event log. Another example involves a manual run of the anti-virus/anti-malware software's update process and verify via the updated version that it is working correctly. Similarly, diagnostic content can verify network settings or process the output of network tests to validate that network settings are good. Typically, diagnostic content will be prioritized to validate aspects with the highest risk, i.e., those that have the highest likelihood of being left in an insecure or broken state in combination with a high impact.

The state validator invocation can happen through a number of different embodiments: manually by the SE, e.g. by pressing the button 134 in a service menu, possibly after a reminder or notification, or be triggered to execute automatically, e.g. when attempting to close the service menu of the medical device, or upon logoff of the user with service credentials, or upon request (e.g., by the SE) of the medical device 120 to return to normal clinical operation (clinical/kiosk/closed profile). The invocation method is selected to optimally integrate in the service engineer workflow and system design.

In one embodiment, the state validator with diagnostic content run in a distributed setting: the state validator runs locally on the medical device 120 and the diagnostic content on a manufacturer support server. The state validator triggers the remote on-demand execution of the diagnostic content. Before or as part of this, this forces a push of log files, etc. to a manufacturer service platform to be used as diagnostic input data. Reception of the data triggers immediate execution of the diagnostic content. Subsequently, results are relayed back to the state validator on the medical device 120 to be used in the feedback to the SE. Alternatively, results are directly communicated to the SE via another communication channel such as email or other authorized communication device or service such as a mobile app.

An advantage of this distributed embodiment is that the existing infrastructure and models (diagnostic content) for reactive and proactive maintenance and security alerting models can be re-used. The difference is that they are executed on-demand instead of per a fixed schedule. A further advantage is that the models (diagnostic content) is always up to date.

In a second embodiment, the state validator with diagnostic content runs locally on the medical device 120. Here, the state validator after being invoked, executes, or interprets the diagnostic content, collects the output, and provides the feedback to the SE, e.g., through the service menu user interface.

For this second embodiment, the state validator regularly retrieves an update for its diagnostic content from a manufacturer support server (e.g., the backend server 111). The update may also include an update of the state validator itself. The update process can take place on-demand every session or at specific intervals. The update provides the advantage that the diagnostic content is up to date including ones that are recently added. Another advantage is that it enables protection of service as explained later.

In both embodiments, an authorization check offers an additional advantage in the form of protection of service. In the first embodiment, the manufacturer support server 111 only executes the diagnostic content if the system or engineer is authorized. Similarly, in the second embodiment, the update server 111 only sends updates if the system or the SE is authorized, e.g., has a service contract or has received the necessary training and credentials. To force this authorization step, the state validator can remove the diagnostic content after each use, forcing an update and authorization check at the next use.

Both the state validator and manufacturer support server 111 log the invocation of the state validator, execution of the diagnostic content, and the results. Hence, data is available to track compliance and effectiveness, e.g., if the state validator is used as intended and feedback taken into consideration.

Advantageously, the state validator and diagnostic content have no side effects on the clinical function. Advantageously, all communication is secured and encrypted.

The following is an example of a use of the system 100. A SE visits the medical device 120 (in this example, an interventional x-ray medical device 120) for service. Using a display and keyboard of the interventional x-ray medical device 120, the SE logs out of a clinical user account currently logged in. The SE logs in under his/her account using a smartcard. The interventional x-ray medical device 120 presents him with service menu options available in service mode, because his credentials entitle access to that functionality.

The SE selects a service menu option on the service mode UI 132 to configure DICOM and HL7. The SE configures a new PACS (Picture Archival and Communication System) with an IP address of the DICOM protocol endpoint on a network. However, when pressing "test connection", the SE finds that the interventional x-ray medical device 120 cannot communicate correctly with the PACS system. The SE suspects that the firewall blocks the communication. In a service menu, the SE selects the host firewall option, which opens the Windows host firewall configuration screen. To quickly troubleshoot, the SE disables the firewall. The SE subsequently determines that the interventional x-ray medical device 120 and PACS system function together as intended.

The SE continues to install additional software. The SE chooses the software installation option in the service menu. The interventional x-ray medical device 120 de-activates its software whitelisting security control to allow for the installation. The SE executes the installer of the new software from his USB stick. In the service menu, the SE selects installation done option, which adds the installed software to the whitelist and re-activates the software whitelisting security control.

The SE subsequently selects the option to logout in the service menu. This ends the service mode, which triggers the interventional x-ray medical device 120 to validate the state thereof. The interventional x-ray medical device 120 (using the state validator) triggers collection of logs (including software whitelisting logs) and querying of configuration (firewall configuration) to validate the state. Next it executes the validation models stored on the interventional x-ray medical device 120.

The software whitelisting validation model finds the whitelisting log data indicating that the security control is (re)enabled and functioning and thereby in a correct state.

However, the firewall validation model fails on the firewall configuration data indicating that the firewall is disabled.

The firewall validation failure (incorrect firewall configuration) is presented on the screen to the SE with the options to remain in service mode or close the service mode regardless. The SE selects remain, and selects the firewall option in the service menu. In the Windows Firewall configuration screen, the SE adds a firewall rule for the IP address and port number of the PACS system as specified by the service manual to enable the connection. Next, the SE enables the firewall. The SE subsequently verifies that the interventional x-ray medical device 120 and PACS system still function together as intended.

The SE subsequently again selects the option to logout. This triggers again the process to validate the state of the interventional x-ray medical device 120. This time the firewall validation model also indicates that the interventional x-ray medical device 120 is not in an incorrect state. The logout proceeds unhindered, and no warning is presented to the SE. The clinical user can login.

A non-transitory storage medium includes any medium for storing or transmitting information in a form readable by a machine (e.g., a computer). For instance, a machine-readable medium includes read only memory ("ROM"), solid state drive (SSD), flash memory, or other electronic storage medium; a hard disk drive, RAID array, or other magnetic disk storage media; an optical disk or other optical storage media; or so forth.

The methods illustrated throughout the specification, may be implemented as instructions stored on a non-transitory storage medium and read and executed by a computer or other electronic processor.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof

The invention claimed is:

1. A non-transitory computer readable medium storing:

instructions readable and executable by at least one electronic processor to provide an operating mode for a medical device to provide medical diagnostic and/or medical treatment functionality;

instructions readable and executable by the at least one electronic processor to provide a service mode for the medical device that provides service functions for servicing the medical device; and instructions readable and executable by the at least one electronic processor to:

perform a validation process at an end of a servicing session of the medical device performed using the service mode to determine whether the medical device is in an incorrect operating state; and display, on a display device operable by a service engineer (SE) and in response to determining the medical device is in the incorrect operating state, an indication that the medical device is in the incorrect operating state.

2. The non-transitory computer readable medium of claim 1, wherein the operating mode is provided on an operating mode user interface (UI) for the medical device that provides operational functions for operating the medical device.

3. The non-transitory computer readable medium of claim 1, wherein the service mode is provided on a service mode user interface (UI) for the medical device that provides service functions for servicing the medical device.

4. The non-transitory computer readable medium of claim 1, wherein the validation process includes:

determining a state of the medical device by analyzing device data generated by the medical device.

5. The non-transitory computer readable medium of claim 1, wherein the validation process includes:

determining a state of the medical device by analyzing a record of operations performed during the servicing session.

6. The non-transitory computer readable medium of claim 1, wherein the validation process includes:

determining a most-recent correct operational state of the medical device; and comparing a current state of the medical device with the most-recent correct operational state of the medical device.

7. The non-transitory computer readable medium of claim 1, wherein the instructions further include:

providing a button selectable by the SE via at least one user input device to perform the validation process.

8. The non-transitory computer readable medium of claim 1, wherein the instructions further include:

automatically performing the validation process responsive to an input to the service mode user interface indicating that the servicing session is completed.

9. The non-transitory computer readable medium of claim 1, wherein the instructions further include:

automatically performing the validation process responsive to the medical device entering the operating mode after the servicing session is completed.

10. The non-transitory computer readable medium of claim 1, wherein the validation process is performed on a central remote server operable by a manufacturer of the medical device.

11. The non-transitory computer readable medium of claim 1, wherein the validation process includes detecting the incorrect operating state comprising anti-virus software of the medical device failing to update virus signatures.

12. The non-transitory computer readable medium of claim 1, wherein the validation process includes detecting the incorrect operating state comprising software whitelisting of the medical device being deactivated or left in an unsupported or insecure configuration setting.

13. The non-transitory computer readable medium of claim 1, wherein the validation process includes detecting the incorrect operating state comprising an incorrectly configured or deactivated firewall of the medical device.

14. The non-transitory computer readable medium of claim 1, wherein the validation process includes detecting the incorrect operating state comprising a configuration of the medical device that is not compatible with operating the medical device to provide the medical diagnostic and/or medical treatment functionality.

15. The non-transitory computer readable medium of claim 1, wherein the validation process includes detecting the incorrect operating state comprising a missing component of the medical device.

16. An electronic device, comprising:

at least one electronic processor; and a non-transitory computer readable medium storing instructions readable and executable by the at least one electronic processor to:

provide an operating mode user interface (UI) for a medical device that provides operational functions for operating the medical device to provide medical diagnostic and/or medical treatment functionality;

perform a validation process at an end of a servicing session of the medical device performed to determine whether the medical device is in an incorrect operating state, wherein the validation process is automatically performed responsive to an input indicating that the servicing session is completed; and display, on a display device operable by the SE and in response to determining the medical device is in the incorrect operating state, an indication that the medical device is in the incorrect operating state.

17. The electronic device of claim 16, wherein the validation process includes:

determining a state of the medical device by analyzing device data automatically generated by the medical device.

18. The electronic device of claim 16, wherein the validation process includes:

determining a state of the medical device by analyzing a record of operations performed during the servicing session.

19. The electronic device of claim 16, wherein the validation process includes:

determining a most-recent operational state of the medical device; and comparing a current state of the medical device with the most-recent operational state of the medical device.

20. A method of determining whether a medical device is in an incorrect operating state following a servicing session, the method comprising:

providing an operating mode user interface (UI) for a medical device that provides operational functions for operating the medical device to provide medical diagnostic and/or medical treatment functionality;

providing a service mode user interface for the medical device that provides service functions for servicing the electronic device;

performing a validation process at an end of a servicing session of the medical device performed using the service mode user interface to determine whether the medical device is in an incorrect operating state, wherein the validation process is automatically performed responsive to the medical device entering the operating mode user interface after the servicing session is completed; and displaying, on a display device of a remote electronic processing device operable by the SE and in response to determining the medical device is in the incorrect operating state, an indication that the medical device is in the incorrect operating state.

* * * * *